(12) United States Patent
Wang et al.

(10) Patent No.: US 8,551,571 B2
(45) Date of Patent: Oct. 8, 2013

(54) METHOD FOR MAKING A CONDUCTIVE POLYMER COMPOSITE FOR DETECTING A SORT OF GAS

(75) Inventors: Li-Chun Wang, Taoyuan County (TW); Yuh Sung, Taoyuan County (TW); Shiaw-Ruey Lin, New Taipei (TW); Cheng-Long Ho, New Taipei (TW); Chang-Ping Chang, New Taipei (TW); Chen-Yu Lin, New Taipei (TW)

(73) Assignee: Chung-Shan Institute of Science and Technology, Armaments Bureau, Dept. of National Defense (TW)

( * ) Notice: Subject to any disclaimer, the term of this patent is extended or adjusted under 35 U.S.C. 154(b) by 138 days.

(21) Appl. No.: 13/293,237

(22) Filed: Nov. 10, 2011

(65) Prior Publication Data
US 2013/0122191 A1    May 16, 2013

(51) Int. Cl.
*B05D 5/12* (2006.01)
*B05D 1/38* (2006.01)

(52) U.S. Cl.
USPC .............. 427/402; 427/331; 427/407.1

(58) Field of Classification Search
USPC ................. 427/331, 402, 407.1
See application file for complete search history.

(56) References Cited

U.S. PATENT DOCUMENTS

| 6,759,010 B2 * | 7/2004 | Lewis et al. ............... 422/82.02 |
| 2006/0233692 A1 * | 10/2006 | Scaringe et al. ............. 423/335 |

* cited by examiner

*Primary Examiner* — Frederick Parker

(57) ABSTRACT

A method for making a conductive polymer composite for detecting a gas includes forming a porous conductive layer of a conductive powder on a substrate, applying a polymer solution containing a solvent and a gas responsive polymer material dissolved in the solvent to the porous conductive layer such that a portion of the polymer solution penetrates into the porous conductive layer and the remainder of the polymer solution forms a thin film covering a top of the porous conductive layer, the gas responsive polymer material being capable of adsorbing and desorbing the gas, and removing the solvent from the polymer solution so as to form a polymer matrix covering the porous conductive layer.

5 Claims, 3 Drawing Sheets

METHOD FOR MAKING A CONDUCTIVE POLYMER COMPOSITE FOR DETECTING A SORT OF GAS

BACKGROUND OF INVENTION

1. Field of Invention

The present invention relates to a method for making a conductive polymer composite and, more particularly, to a method for making a conductive polymer composite for detecting a sort of gas.

2. Related Prior Art

Referring to FIG. 1, a sensor for detecting a sort of gas was disclosed by Keat Ghee Ong, IEEE Sensors Journal, vol. 2, No. 2, April 2002. The sensor includes a substrate 10, electrodes 11 provided on the substrate 10, an insulating layer 12 provided on the substrate 10, and a conductive composite film 13 provided on the insulating layer 12. To make the conductive composite film 13, multi-walled carbon nanotubes 131 are evenly mixed with silicon dioxide solution, and the mixture is coated on the insulating layer 12 and dried so that water is removed from the mixture. Thus, the conductive composite film 13 includes multiple conductive paths. Some of the multi-walled carbon nanotubes 131 stick out from the silicon dioxide base 132. Thus, the multi-walled carbon nanotubes 131 that stick out of the silicon dioxide base 132 attract a sort of gas so that the dielectric constant and conductivity of the multi-walled carbon nanotubes 131 are changed and that the concentration of the sort of gas is detected.

Another sensor for detecting a sort of gas was disclosed by Jose K. Abraham, Smart Material Structure, 13, (2004) 1045-1049. The sensor includes a circuit board, electrodes provided on the circuit board, and a conductive composite coating provided on the circuit board. To make the conductive composite coating, carbon nanotubes are mixed with gas responsive polymer such as polymethylmethacrylate ("PMMA") are evenly mixed with each other in a solvent by ultrasonic waves, and the mixture is coated on the circuit board and dried to remove the solvent from the mixture. Thus, on the circuit board, there is formed a conductive composite coating similar to the conductive composite film shown in FIG. 1. The polymer attracts a sort of gas so that it expands and changes the conductive paths of the carbon nanotubes on the polymer base and the resistance so that the concentration of the sort of gas is detected. Some of the carbon nanotubes that stick out of the polymer however also attract the sort of gas and change the conductive paths thereof. Thus, the detection of concentration of the sort of gas is complicated, the reproducibility is poor, and errors could easily occur.

A sensor array has been disclosed in U.S. Pat. No. 6,759,010. The sensor array includes various sensors for detecting the concentrations of different substances. The disclosure of U.S. Pat. No. 6,759,010 is incorporated in the present application.

The present invention is therefore intended to obviate or at least alleviate the problems encountered in prior art.

SUMMARY OF INVENTION

It is the primary objective of the present invention to provide a method for making a reliable conductive polymer composite for detecting a sort of gas.

To achieve the foregoing objective, the method includes the step of forming a porous conductive layer of conductive powder on a substrate. Then, polymer solution is provided on the porous conductive layer so that some of the polymer solution penetrates the porous conductive layer while the other polymer solution forms a film over the porous conductive layer. The polymer solution includes solvent and gas responsive polymer dissolved in the solvent. The gas responsive polymer can execute adsorption and desorption of the sort of gas. Then, the solvent is removed from the polymer solution provided on the porous conductive layer to form, on the substrate, a polymer base that encompasses the porous conductive layer.

Other objectives, advantages and features of the present invention will be apparent from the following description referring to the attached drawings.

BRIEF DESCRIPTION OF DRAWINGS

The present invention will be described via detailed illustration of the preferred embodiment versus the prior art referring to the drawings wherein.

DETAILED DESCRIPTION OF EMBODIMENTS

Figure 1:
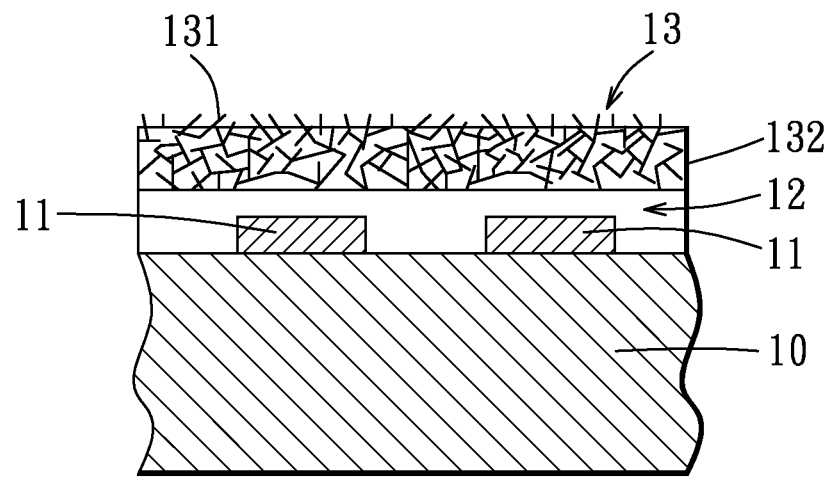
FIG. 1 is a partial, cross-sectional view of a conventional conductive polymer composite for detecting a sort of gas.
Figure 2:
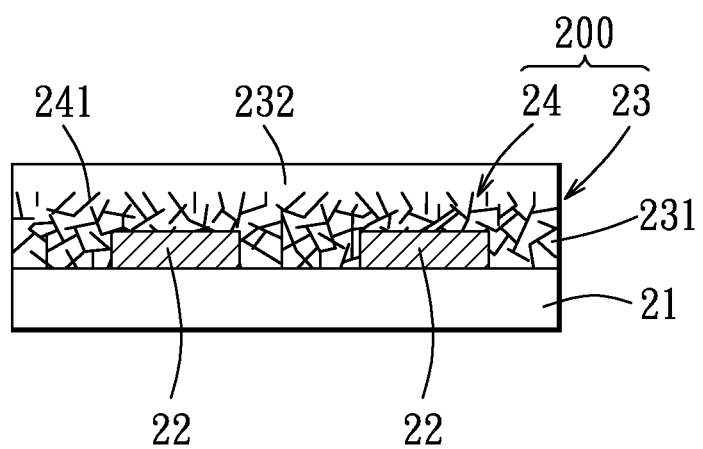
FIG. 2 is a cross-sectional view of a reliable conductive polymer composite for detecting a sort of gas according to the present invention.

Referring to FIG. 2, there is shown a conductive polymer composite for detecting a sort of gas according to the present invention. The conductive polymer composite includes a substrate 21, a porous conductive layer 24 and a polymer base 23.

The substrate 21 is made with two electrodes 22. Preferably, the substrate 21 is a ceramic disc or silicon wafer formed with an insulating layer of silicon dioxide.

The porous conductive layer 24 is made of conductive powder 241 that is paved on the substrate 21 so that the porous conductive layer 24 is made with many conductive paths. The conductive powder 241 may be metal grains or conductive inorganic grains. Alternatively, the conductive powder 241 may be carbon black powder or carbon nanotubes. Preferably, the conductive powder 241 is carbon nanotubes. Preferably, the carbon nanotubes are multi-walled carbon nanotubes.

The polymer base 23 is provided on and over the porous conductive layer 24. The polymer base 23 is made of a sort of gas responsive polymer. The polymer base 23 includes a lower portion 231 and an upper portion 232. The lower portion 231 of the polymer base 23 penetrates and encompasses the porous conductive layer 24. The upper portion 232 of the polymer base 23 covers the lower portion 231 of the polymer base 23 and therefore the porous conductive layer 24. The thickness of the lower portion 231 of the polymer base 23 is about 600 nm. The thickness of the upper portion 232 of the polymer base 23 is about 400 nm.

In operation, the gas responsive polymer of the polymer base 23 attracts a sort of gas and expands and cut some of the conductive paths of the porous conductive layer 24. Thus, the resistance of the conductive polymer composite is increased. Therefore, the concentration of the sort of gas is determined by measuring the change in the resistance of the conductive polymer composite.

Figure 3:
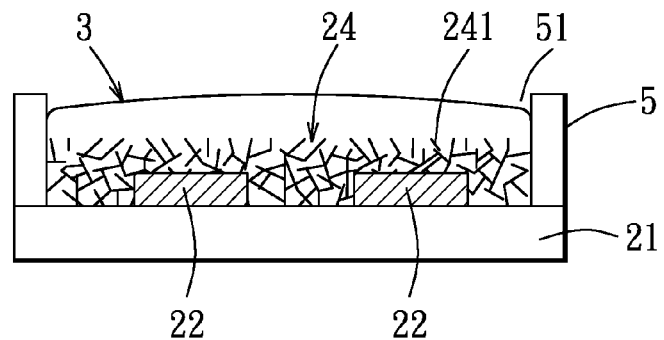
FIGS. 3 through 5 show a method for making the conductive polymer composite shown in FIG. 2.
Figure 4:
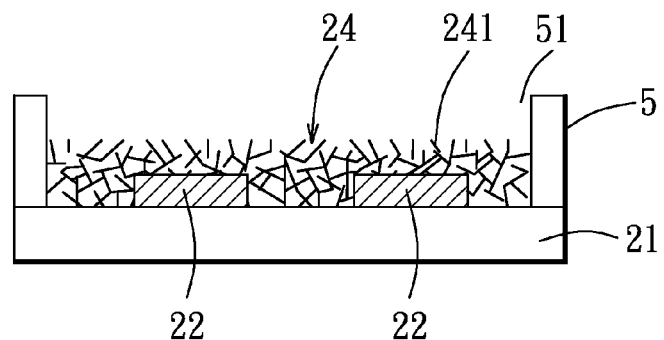
Figure 5:
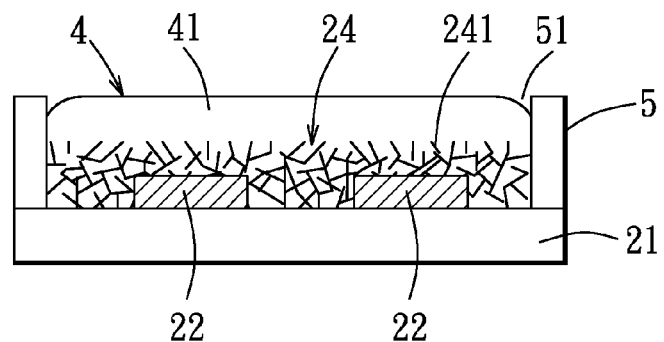

Referring to FIGS. 3 through 5, there is shown a method for making the conductive polymer composite shown in FIG. 2.

Referring to FIG. 3, at first, powder-containing mixture 3 is provided on the substrate 21. The powder-containing mixture 3 includes the conductive powder 241 evenly distributed in solvent 31. Preferably, the concentration of the conductive powder 241 in the powder-containing mixture 3 is 0.1 wt % to 2 wt %.

Referring to FIG. 4, the solvent 31 is removed from the powder-containing mixture 3 provided on the substrate 21. Thus, the porous conductive layer 24 is made of the conductive powder 241 that is paved on the substrate 21.

Referring to FIG. 5, polymer solution 4 is provided on the porous conductive layer 24 so that some of the polymer solution 4 penetrates the porous conductive layer 24 while the other polymer solution 4 forms a thin film over the porous conductive layer 24. The polymer solution 4 includes the gas responsive polymer dissolved in solvent 41. The gas responsive polymer attracts the sort of gas.

Finally, the solvent 41 is removed from the polymer solution provided on the porous conductive layer 24, thus leaving the polymer base 23 over the porous conductive layer 24 that is provided on the substrate 21.

Preferably, the concentration of the gas responsive polymer in the polymer solution is 0.5 wt % to 5 wt %. Preferably, the concentration of the gas responsive polymer in the polymer solution is 0.5 wt % to 2 wt %.

The gas responsive polymer may be styrene/allyl alcohol copolymer ("SAA"), polyvinylpyrrolidone, poly(methyl vinyl ether-alt-maleic acid), poly(alpha-methylstyrene), hydroxypropyl methyl cellulose, poly(ethylene adipate), poly(vinyl benzy chloride), polycarbonate, polystyrene, ethyl cellulose, polyethylene glycol, polymethylmethacrylate, poly(vinylidene chloride-co-acrylonitrile), poly(ethylene oxide), poly(4-vinylphenol-co-methyl methacrylate), polyethyleneimine, poly(vinylpropinoate), poly(epichlorhydrin), poly(isobutylene), polymethyltrifluoropropylsiloxane, polyisoprene, 75%-phenyl-25%-methylpolysiloxane, poly (2,3-dibutoxy-1,4-benzyl ethylene), polyvinylcarbazole or poly(2-methoxy-5-(2'-ethyl hexthoxy)-p-benzyl ethylene), taken alone or in any combination.

The solvent of the polymer solution may be water, ethanol, acetone, toluene, dimethylformamide or tetrahydrofuran, taken alone or in any combination.

The solvent of the powder-containing mixture may be water, isopropanol, polyvinyl alcohol or methyl ethyl ketone, taken alone or in any combination.

The method of the present invention can be used to make a sensor array that includes a plurality of the polymer composite. The structure of the sensor array may be similar to the structure of the sensor array that is disclosed in U.S. Pat. No. 6,759,010.

Embodiments of the present invention and their effects will be discussed later. The embodiments are made, tested or evaluated by chemicals and pieces of equipment to be described. These things are conducted at the normal temperature under the normal pressure unless otherwise described. It should be noted that these embodiments are described for exemplary purposes, not for limiting the scope of the present invention.

First Embodiment (E1)

In the first embodiment, to make the conductive polymer composite for sensing a sort of gas, the carbon nanotubes are deposited on the substrate via chemical vapor deposition. The external diameter of the carbon nanotubes is 10 to 20 nm. The carbon nanotubes are scraped from substrate and become powder. The powder made of the carbon nanotubes are evenly dissolved in methyl ethyl ketone, the solvent, to provide the powder-containing mixture 3 in which the concentration of the carbon nanotubes is about 1 wt %.

A pipette is used to provide 0.5 to 2 µl of the powder-containing mixture 3 onto the silicon of the substrate 21 that is a silicon wafer formed with an insulating layer of silicon dioxide and provided with the electrodes 22. On the substrate 21, there is formed a quantitative film 5 that includes an aperture defined therein (FIG. 3). The powder-containing mixture 3 is filled in the aperture. Thus, the amount of the powder-containing mixture 3 provided on the substrate 21 is controlled by the size of the aperture.

The substrate 21 is dried in an oven at 50° C. for 3 hours to remove the methyl ethyl ketone, the solvent, and form the porous conductive layer 24 on the substrate 21. The porous conductive layer 24 includes a conductive path connected to the electrodes 22 (FIG. 4).

Gas responsive polymer-polystyrene is dissolved in tetrahydrofuran to provide polymer solution 4 in which the concentration of the polystyrene is about 1 wt %. A pipette is used to provide about 0.5 to 2 µl of the polymer solution 4 onto the porous conductive layer 24 so that some of the polymer solution 4 penetrates the porous conductive layer 24 and the other polymer solution 4 covers the porous conductive layer 24.

The polymer solution 4 is filled in the aperture defined in the quantitative film 5 (FIG. 5). The amount of the polymer solution 4 provided on the porous conductive layer 24 is controlled via the size of the aperture. The substrate 21 is dried in an oven at 50° C. for 3 hours to remove the solvent and form the polymer base 23 that encompasses the porous conductive layer 24. The polymer base 23 is made with the lower portion 231 that is about 600 nm thick and encompasses the porous conductive layer and the upper portion 232 that is about 400 nm thick and covers the porous conductive layer.

Second to Sixth Embodiments (E2-E6)

The second to sixth embodiments are identical to the first embodiment except that the concentrations of the polystyrene are 0.5 wt %, 2 wt %, 3 wt %, 4 wt % and 5 wt %.

The conductive polymer composite according to the first to sixth embodiments are used to adsorb methanol gas continuously and then tested. Each of the tested conductive polymer composite is provide in a reaction chamber at the room temperature. For adsorption, 1000 ppm methanol gas is introduced into and out of the reaction chamber at 200 cc/min for 2 minutes. Then, for desorption, instead of the methanol gas, air is directed through the reaction chamber for 10 minutes. In the adsorption and desorption, the resistance is measured continuously to provide a curve of the resistance of the conductive polymer composite versus time in the reaction.

Figure 6:
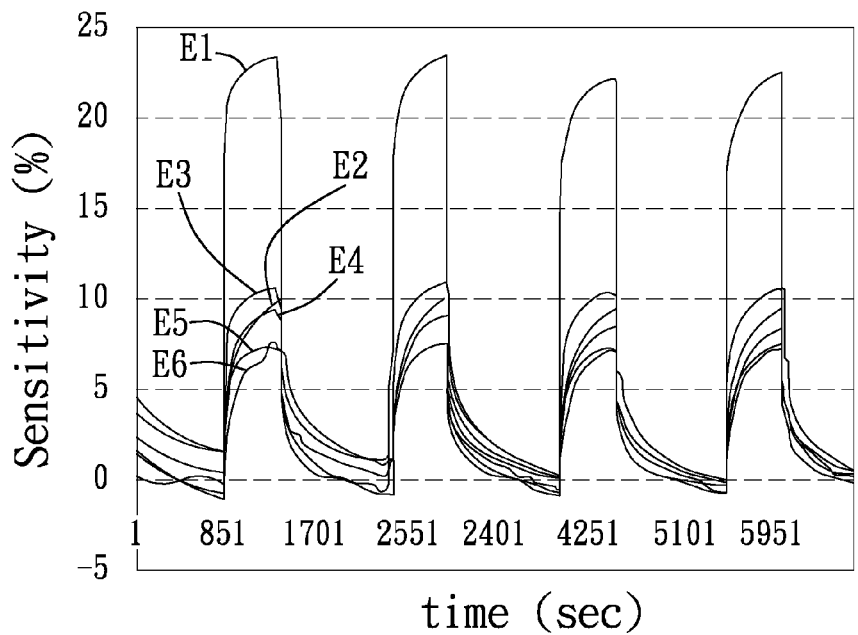
FIG. 6 is a chart for showing the sensitivities for methanol of six embodiments of the present invention.

Referring to FIG. 6, the results of the tests of the conductive polymer composite adsorbing the methanol are shown. The responsiveness S is calculated by the following equation:

$$S=(R-R_0)/R_0$$

wherein $R_0$ is the resistance of the conductive polymer composite before adsorbing the methanol, and R is the resistance of the conductive polymer composite after adsorbing the methanol. Where the concentration of the polystyrene is about 1 wt %, the responsiveness of the conductive polymer composite is the highest.

FIRST COMPARED EXAMPLE (CE1)

The first compared example is like the first embodiment except that the powder-containing mixture is mixed with polymer solution to provide a blended material. A pipette is used to provide about 0.5 to 2 µl of the blended material onto the substrate. Then, the blended material is dried to provide the conductive polymer composite.

In comparison, the first compared example and the first embodiment are used to adsorb methanol gas continuously and then tested.

Figure 7:
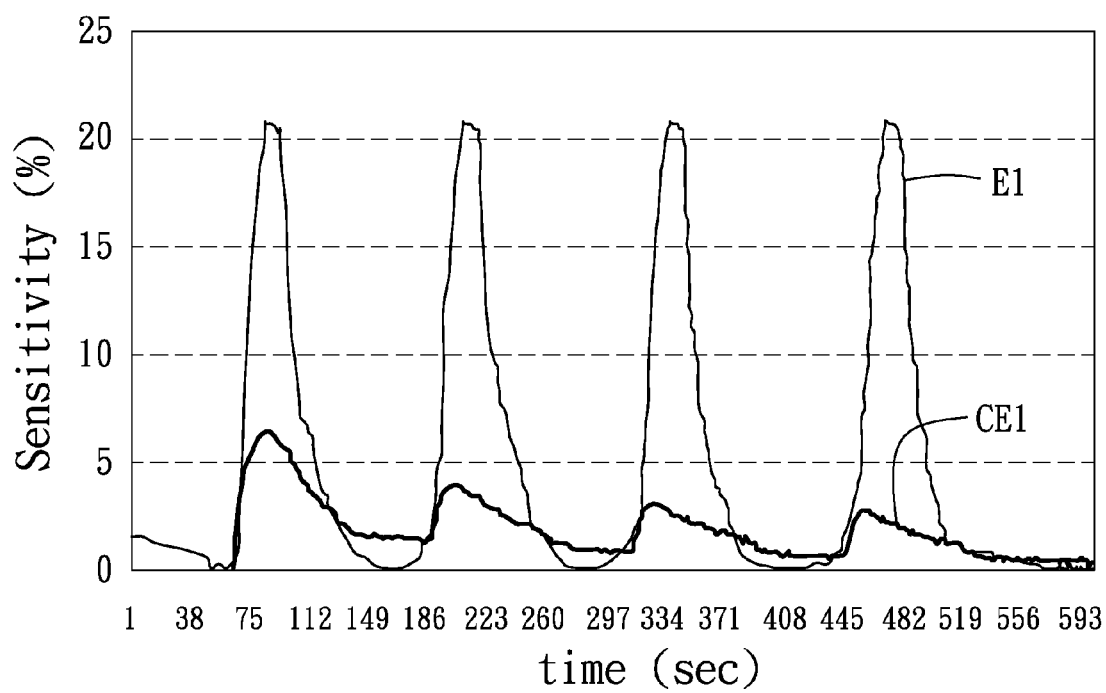
FIG. 7 is a chart for showing the sensitivity for methanol of the first embodiment of the present invention versus the prior art.

Referring to FIG. 7, the results of the tests of the first embodiment versus the first compared example are shown. The responsiveness of the first compared example is low and decreases as time elapses in comparison with the responsiveness of the first embodiment that is high and does not drop considerably as time elapses.

As discussed above, the method for making a conductive polymer composite for sensing a sort of gas according to the present invention improves the responsiveness and reproducibility.

The present invention has been described via the detailed illustration of the preferred embodiment. Those skilled in the art can derive variations from the preferred embodiment without departing from the scope of the present invention. Therefore, the preferred embodiment shall not limit the scope of the present invention defined in the claims.

The invention claimed is:

1. A method for making a conductive polymer composite for sensing a sort of gas, the method including the steps of:
    forming a porous conductive layer of conductive powder on a substrate;
    applying a polymer solution to the porous conductive layer so that a portion of the polymer solution penetrates into the porous conductive layer and the remainder of polymer solution forms a film over the porous conductive layer, wherein the polymer solution includes solvent and gas responsive polymer dissolved in the solvent, wherein the gas responsive polymer can execute adsorption and desorption of the gas of interest; wherein the concentration of the gas responsive polymer in the polymer solution ranges from 0.5 wt % to 2 wt %; and
    removing the solvent from the polymer solution applied to the porous conductive layer so as to form, on the substrate, a polymer base that covers the porous conductive layer;
    wherein the step of forming the porous conductive layer on the substrate includes the steps of:
    applying a powder-containing mixture to the substrate, the powder-containing mixture includes a solvent and conductive powder dispersed uniformly in the solvent; and
    removing the solvent from the powder-containing mixture applied to the substrate so as to form the porous conductive layer on the substrate; wherein the concentration of the conductive powder in the powder-containing mixture ranges from 0.1 wt % to 2 wt %.

2. The method according to claim 1, wherein the gas responsive polymer includes at least one material selected from the group consisting of styrene/allyl alcohol copolymer ("SAA"), polyvinylpyrrolidone, poly(methyl vinyl ether-alt-maleic acid), poly(alpha-methylstyrene), hydroxypropyl methyl cellulose, poly(ethylene adipate), poly(vinyl benzy chloride), polycarbonate, polystyrene, ethyl cellulose, polyethylene glycol, polymethylmethacrylate, poly(vinylidene chloride-co-acrylonitrile), poly(ethylene oxide), poly(4-vinylphenol-co-methyl methacrylate), polyethyleneimine, poly(vinylpropinoate), poly(epichlorhydrin), poly(isobutylene), polymethyltrifluoropropylsiloxane, polyisoprene, 75%-phenyl-25%-methylpolysiloxane, poly (2,3-dibutoxy-1,4-benzyl ethylene), polyvinylcarbazole and poly(2-methoxy-5-(2'-ethyl hexthoxy)-p-benzyl ethylene).

3. The method according to claim 1, wherein the solvent of the polymer solution includes at least one material selected from the group consisting of water, ethanol, acetone, toluene, dimethylformamide and tetrahydrofuran.

4. The method according to claim 1, wherein the conductive powder includes carbon nanotubes.

5. The method according to claim 1, wherein the solvent of the powder-containing mixture includes at least one material selected from the group consisting of water, isopropanol, polyvinyl alcohol and methyl ethyl ketone.

* * * * *